(12) United States Patent
Frost (10) Patent No.: US 6,372,461 B1
(45) Date of Patent: Apr. 16, 2002

(54) SYNTHESIS OF VANILLIN FROM A CARBON SOURCE

(75) Inventor: John W. Frost, Okemos, MI (US)

(73) Assignee: Board of Directors operating Michigan State University, East Lansing, MI (US)

( * ) Notice: Subject to any disclaimer, the term of this patent is extended or adjusted under 35 U.S.C. 154(b) by 0 days.

(21) Appl. No.: 09/397,720

(22) Filed: Sep. 16, 1999

Related U.S. Application Data (60) Provisional application No. 60/100,937, filed on Sep. 18, 1998.

(51) Int. Cl.[7] .......................... C12N 15/00; C12N 01/20
(52) U.S. Cl. ................ 435/156; 435/320.1; 435/252.33
(58) Field of Search .............................. 435/156, 320.1, 435/252.33

(56) References Cited

U.S. PATENT DOCUMENTS

| | | | | |
|---|---|---|---|---|
| 5,279,950 A | | 1/1994 | Laduda et al. ............... | 435/147 |
| 5,629,181 A | * | 5/1997 | Frost et al. .................. | 435/156 |
| 5,795,759 A | * | 8/1998 | Rosazza et al. ............. | 435/189 |

OTHER PUBLICATIONS

Campbell, C.J. et al., "The End of Cheap Oil," *Sci. Am.* 278(3):77–83 (1998).

Clark, G.S., "Vanillin," *Perfum. Flavor.* 15:45–54 (1990).

Coward, J.K. et al., "Kinetic Studies on Catechol O–Methyltransferase. Product Inhibition and the Nature of the Catechol Binding Site," *Biochemistry* 12(12):2291–2297 (1973).

Esposito, L. et al., "Vanillin," *Kirk–Othmer Encyclopedia of Chemical Technology*, Fourth Ed., Kroschwitz, J.I., Howe–Grant, M., Ed., Wiley: New York, vol. 24:812–925 (1997).

Falconnier, B. et al., "Vanillin as a product of ferulic acid biotransformation by the white–rot fungus *Pycnoporus cinabarinus* I–937: Identification of metabolic pathways," *J. Biotechnol.* 37:123–132 (1994).

Gross, G.G. et al., "Reduction of Cinnamic Acid to Cinnamaldehyde and Alcohol," *Biochem. Biophy. Res. Commun.* 32(2):173–178 (1968).

Gross, G.G. et al., "Reduktion aromatischer Sauren zu Aldehyden und Alkoholen im zellfreien System," *Eur. J. Biochem.* 8:413–419 (1969).

Gross, G.G., "Formation and Reduction of Intermediate Acyladenylate by Acryl–Aldehyde," *Eur. J. Biochem.* 31:585–592 (1972).

Lesage–Meessen, L. et al., "A two–step bioconversion process for vanillin production from ferulic acid combining *Aspergillus niger* and *Pycnoporus cinnabarinus*," *J. Biotechnol.* 50:107–113 (1996).

Lesage–Meessen, L. et al., "An attemp to channel the transformation of vanillic acid into vanillin by controlling methoxyhydroquinone formation in *Pycnoporus cinnabarinus* with cellobiose," *Appl. Microbiol. Biotechnol.* 47:393–397 (1997).

Ranadive, A.S., "Vanilla—Cultivation, Curing, Chemistry, Technology and Commercial Products," In *Spices, Herbs, and Edible Fungi*, Charalambous, G., Ed., Elsevier: Amsterdam, pp. 517–577 (1994).

Snell, K. et al., "Synthetic Modification of the *Escherichia coli* Chromosome: Enhancing the Biocatalytic Conversion of Glucose into Aromatic Chemicals," *J. Am. Chem. Soc.* 118(24):5605–5614 (1996).

Westcott, R.J. et al., "Use of Organized Viable Vanilla Plant Aerial Roots for the Production of Natural Vanillin," *Phytochemistry* 35(1):135–138 (1994).

Zenk, M.H. et al., "The Enzymic Reduction of Cinnamic Acids," *Recent Adv. Phytochem.* 4:87–106 (1972).

Tuomainen et al. "Validation of assay of catechol–O–methyltransferase activity in human erythrocytes", (1996), J Pharm Biomed Anal 14:515–523.*

Weaver et al. "Cloning of an aroF allele encoding a tyrosine insensitive 3–deoxy–D–arabino–heptulosonate 7–phosphate synthase", (1990) J Bacteriol 172:6581–6584.*

Guldberg, H.A. et al., "Catechol–O–Methyl Transferase: Pharmacological Aspects and Physiological Role," *Pharmacological Reviews* 27(2):135–206 (1975).

Reenila, I. et al., "Opposite Effect of Ethanol on Recombinant Membrane–Bound and Soluble Activities of Catecho-l–O–methyltransferase," *Pharmacology & Toxicology* 77:414–416 (1995).

* cited by examiner

Primary Examiner—Rebecca E. Prouty
Assistant Examiner—David Steadman
(74) *Attorney, Agent, or Firm*—Harness, Dickey & Pierce, P.L.C.

(57) ABSTRACT

A bioengineered synthesis scheme for the production of vanillin from a carbon source is provided. The bioconversion methods of the present invention comprise the steps of microbe-catalyzed conversion of a carbon source to vanillic acid followed by enzyme-catalyzed reduction of the vanillic acid to produce vanillin. As shown in the synthesis scheme of FIG. 2, the microbe-catalyzed conversion step of the present invention requires five enzymes which are provided by a recombinant microbe. In a preferred embodiment, the recombinant microbe is *Escherichia coli* designed to cause dehydration of 3-dehydroshikimic acid and regioselective methylation of the resulting protocatechuic acid. The enzyme-catalyzed reduction step of the present invention comprises the reduction of vanillic acid to vanillin by aryl-aldehyde dehydrogenase.

26 Claims, 4 Drawing Sheets

<sup>a</sup> KL7/pKL5.26A or KL7/pKL5.97A; <sup>b</sup> *N. crassa* aryl-aldehyde dehydrogenase; <sup>c</sup> microbial catabolism; <sup>d</sup> HCO₃H, HCO₂H; <sup>e</sup> Me₂SO₄; <sup>f</sup> i) HCOCO₂H, ii) O₂; iii) H⁺; <sup>g</sup> UDP-glucose:coniferyl alcohol glucosyltransferase; <sup>h</sup> unidentified enzymes; <sup>i</sup> β-glucosidase.

Figure 1 a 3-deoxy-D-*arabino*-heptulosonic acid 7-phosphate synthase (*aroF*$^{FBR}$); b 3-dehydroquinate synthase (*aroB*); c 3-dehydroquinate dehydratase (*aroD*); d 3-dehydroshikimate dehydratase (*aroZ*); e catechol-*O*-methyltransferase (*COMT*); f aryl-aldehyde dehydrogenase; g D-glucose 6-phosphate dehydrogenase, D-glucose 6-phosphate; SAM: *S*-adenosylmethionine; SAH: *S*-adenosylhomocysteine.

$^1$H NMR of vanillin synthesized from glucose. Vanillin resonances: δ 9.63 (s, 1H), 7.46 (d, J = 8 Hz, 1H), 7.39 (s, 1H), 6.98 (d, J = 8 Hz, 1H), 3.88 (s, 3H); Isovanillin resonances: δ 9.65 (s, 1H), 7.48 (d, J = 8 Hz, 1H), 7.29 (s, 1H), 7.10 (d, J = 8 Hz, 1H), 3.94 (s, 3H).

Figure 4

SYNTHESIS OF VANILLIN FROM A CARBON SOURCE

This application claims benefit of provisional application No. 60/100,937, filed Sep. 18, 1998.

Work on this invention was sponsored in part by the United States Department Of Agriculture Grant No. 95-37500-1930 and the National Science Foundation Grant No. CHE963368 amendment 002. The Government may have certain rights in the invention.

FIELD OF THE INVENTION

The present invention is related to the bioconversion of a carbon source to vanillin and more particularly, to methods of producing vanillin from a carbon source by microbe-catalyzed conversion of the carbon source to vanillic acid and enzyme-catalyzed reduction of vanillic acid to produce vanillin.

BACKGROUND OF THE INVENTION

Figure 1:
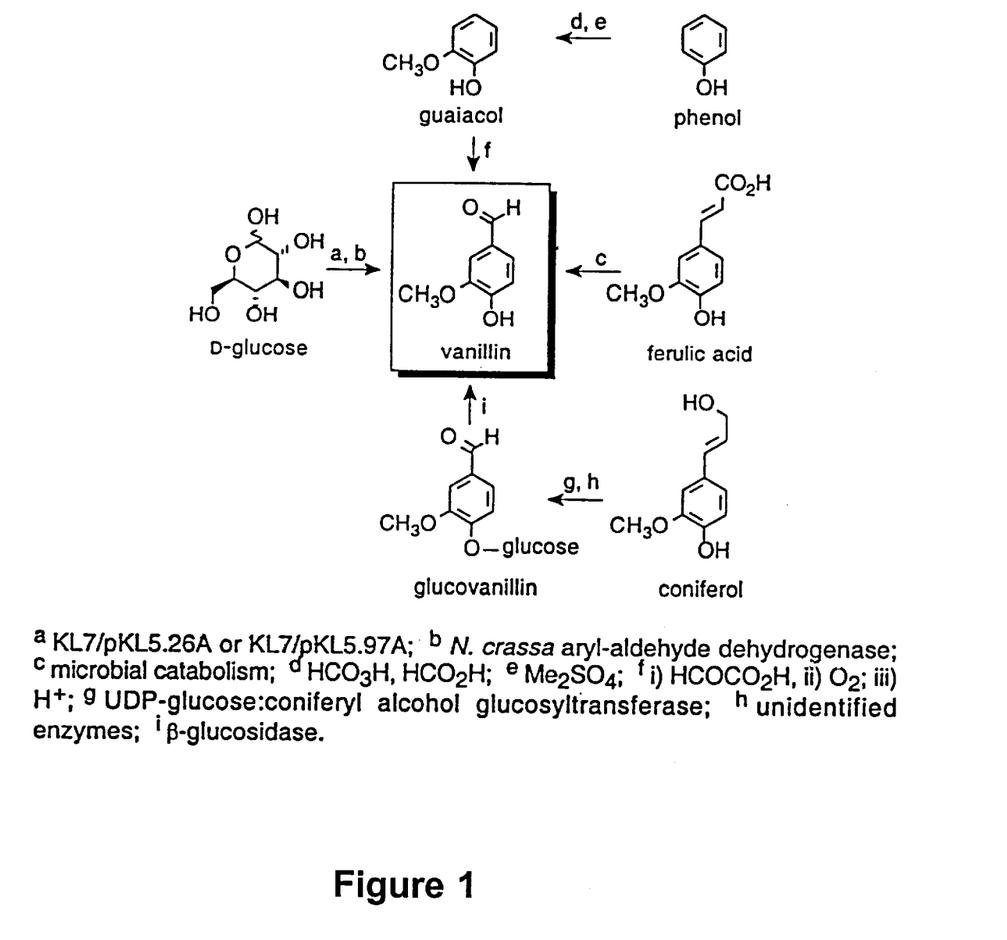
FIG. 1 is a schematic illustrating various synthesis schemes for producing vanillin.

Natural vanillin is produced from glucovanillin (FIG. 1) when the beans of the orchid *Vanilla planifolia* are submitted to a multi-step curing process. Ranadive, A. S., In *Spices, Herbs, and Edible Fungi*, Charalambous, G., Ed., Elsevier: Amsterdam, p. 517 (1994). Because of the extreme care that must be exercised during vine cultivation, bean harvesting, and hand pollination of flowers, natural vanillin can supply only $2 \times 10^4$ kg/yr of the world's $1.2 \times 10^7$ kg/yr demand for vanillin. Clark, G. S., *Perfum. Flavor.* 15:45 (1990). This has resulted in substitution of synthetic vanillin for natural vanilla in most flavoring applications. Condensation of glyoxylic acid with benzene-derived guaiacol (FIG. 1) is therefore currently the dominant route for vanillin manufacture. Ranadive, A. S., In *Spices, Herbs, and Edible Fungi*, Charalambous, G., Ed., Elsevier: Amsterdam, p. 517 (1994); Clark, G. S., *Perfum. Flavor.* 15:45 (1990); Esposito, L. et al., *Kirk-Othmer Encyclopedia of Chemical Technology*, Fourth Ed., Kroschwitz, J. I.; Howe-Grant, M., Ed.; Wiley: New York, Vol. 24:812 (1997). Limited vanilla bean supplies have also led to extensive research into the use of plant tissue culture and microbes to convert ferulic acid (FIG. 1) into vanillin suitable for labelling as a natural or nature-equivalent flavoring. Falconnier, B. et al., *J. Biotechnol.* 37:123 (1994); Lesage-Meessen, L. et al., *J. Biotechnol.* 50:107 (1996); Lesage-Meessen, L. et al., *Appl. Microbiol. Biotechnol.* 47:393 (1997); Labuda, I. M. et al., U.S. Pat. No. 5,279,950 (1994); Westcott, R. J. et al., *Phytochemistry* 35:135 (1994).

Vanillin is second only to aspartame in terms of market size for a food additive. Vanilla extract derived from *V. planifolia* pods has the advantage of being labeled as a natural flavoring. However, as described above, only relative small volumes of vanilla flavoring can be derived from *V. planifolia* cultivation. Synthesis of vanillin from benzene-derived guaiacol is therefore the basis of large-scale industrial manufacture of vanillin. This vanillin however, can not be labeled as a natural flavoring and synthesis of vanillin from benzene-derived guaiacol is not environmentally benign. With respect to the ferulate-derived vanillin, although it can be labeled as a natural flavoring, the microbes and cultured plant cells used to process the ferulic acid give low titers of vanillin (approximately 1 g/L). Falconnier, B. et al., *J. Biotechnol.* 37:123 (1994); Lesage-Meessen, L. et al., *J. Biotechnol.* 50:107 (1996); Lesage-Meessen, L. et al., *Appl. Microbiol. Biotechnol.* 47:393 (1997); Labuda, I. M. et al., U.S. Pat. No. 5,279,950 (1994); Westcott, R. J. et al., *Phytochemistry* 35:135 (1994). A further problem is the availability of ferulic acid; although corn fiber is rich in ferulic acid esters, no process amenable to commercial scale isolation and processing of this ferulic acid has been developed.

It would thus be desirable to provide a method for synthesizing vanillin. It would further be desirable to provide a method for synthesizing vanillin which is economically attractive. It would also be desirable to provide a method for synthesizing vanillin which is environmentally benign. It would further be desirable to provide a method for synthesizing vanillin which utilizes an abundant, renewable resource as the starting material.

SUMMARY OF THE INVENTION

A bioengineered synthesis scheme for the production of vanillin from a carbon source is provided. In one embodiment, the bioconversion methods of the present invention comprise the steps of microbe-catalyzed conversion of a carbon source to vanillic acid followed by enzyme-catalyzed reduction of vanillic acid to produce vanillin. As shown in the synthesis scheme of FIG. 2, the microbe-catalyzed conversion step of the present invention requires five enzymes which are provided by a recombinant microbe. In a preferred embodiment, the recombinant microbe is *Escherichia coli* designed to cause dehydration of 3-dehydroshikimic acid and regioselective methylation of the resulting protocatechuic acid. The enzyme-catalyzed reduction step of the present invention comprises the reduction of vanillic acid to vanillin by aryl-aldehyde dehydrogenase. In a preferred embodiment, the aryl-aldehyde dehydrogenase is purified from *Neurospora crassa*.

The biocatalytic synthesis of vanillin provided herein is environmentally benign, economically attractive, and utilizes abundant renewable sources, as starting materials.

Additional objects, advantages, and features of the present invention will become apparent from the following description and appended claims, taken in conjunction with the accompanying drawings.

BRIEF DESCRIPTION OF THE DRAWINGS

The various advantages of the present invention will become apparent to one skilled in the art by reading the following specification and subjoined claims and by referencing the following drawings in which:

DETAILED DESCRIPTION OF THE PREFERRED EMBODIMENTS

A bioengineered synthesis scheme for the production of vanillin from a carbon source is provided herein. Methods of producing vanillin from a carbon source based on the synthesis scheme are also provided. In one embodiment, a method is provided wherein the carbon source is converted to vanillic acid by a recombinant microbe followed by the reduction of vanillic acid to vanillin by aryl-aldehyde dehydrogenase. In a preferred embodiment, the aryl-aldehyde dehydrogenase is isolated from *Neurospora crassa*.

Although microbe-catalyzed conversion of a carbon source to vanillic acid followed by enzyme-catalyzed reduction of vanillic acid to vanillin is described in detail herein, in an alternative embodiment, a single recombinant microbe may is employed to convert a carbon source to vanillic acid as well as reduce the vanillic acid to vanillin, e.g., the vanillic acid-synthesizing microbe may also express aryl-aldehyde dehydrogenase. This "single-microbe conversion" may be carried out by any type of microbe sufficiently engineered to produce the desired outcome, including, but not limited to, E. coli, Klebsiella, Neurospora, Nocardia and Saccharomyces.

In another embodiment, vanillic acid synthesized from a carbon source by one microbe is reduced to vanillin by a second microbe, wherein the second microbe expresses aryl-aldehyde dehydrogenase. This "double-microbe conversion" may also be carried out by various types of microbes sufficiently engineered to produce the desired outcome. Neurospora and Nocardia are preferred as the second microbe, as both are known to naturally express aryl-aldehyde dehydrogenase.

In yet another embodiment, the microbe-catalyzed conversion of the carbon source is to 3-dehydroshikimic acid followed by conversion of the 3-dehydroshikimic acid to vanillin. In a further embodiment, the microbe-catalyzed conversion of the carbon source is to protocatechuic acid, followed by conversion of the protocatechuic acid to vanillin. The conversion of 3-dehydroshikimic acid and/or protocatechuic acid to vanillin may be carried out by a second recombinant microbe engineered to provide such a conversion.

The bioconversion methods of the present invention are carried out under conditions of time, temperature, pH, nutrient type and concentration, aeration conditions, methionine supplementation, and limited glucose concentrations, to provide maximal conversion of the carbon source to vanillin. As described in detail in Specific Example 1, in a preferred embodiment, a fed-batch fermentor is used to convert the carbon source to vanillic acid, followed by organic extraction of vanillic acid, e.g., acidification of the fermentation broth and extraction with organic solvent. The fed-batch fermentor process and organic extraction methods are also known to those skilled in the art.

As used herein, the phrase "carbon source" is meant to include biomass derived carbon sources including, but not limited to, xylose, arabinose, glucose and the intermediates (e.g., dicarboxylic acids) in the Krebs cycle, either alone or in combination. In a preferred embodiment, the carbon source is glucose.

In one embodiment, the recombinant microbe E. coli is employed in the methods of the present invention. In a preferred embodiment, the E. coli comprises a mutated aroE locus and an aroB/aroZ cassette inserted into the serA locus. This recombinant E. coli, designated KL7, may further comprise a plasmid carrying an aroF$^{FBR}$ insert, a serA insert and a P$_{tac}$ COMT loci. The lack of aroE-encoded shikimate dehydrogenase results in synthesis of 3-dehydroshikimic acid. It will be appreciated, however, that the aroE locus mutation is not essential and is employed to ensure sufficient 3-dehydroshikimic acid formation. The 3-dehydroshikimic acid is converted into protocatechuic acid by genome-localized, aroZ-encoded 3-dehydroshikimate dehydratase. Plasmid-localized P$_{tac}$COMT encodes catechol-O-methyltransferase for conversion of protocatechuic acid into vanillic acid. In addition, the two copies of aroB increase 3-dehydroquinate synthase activity to the point where the enzyme no longer impedes carbon flow. Snell, K. et al., *J. Am. Chem. Soc.* 118:5605 (1996).

In a preferred embodiment, the recombinant *E. coil* comprises plasmid pKL5.97A carrying an aroF$^{FBR}$ insert, a serA insert and two P$_{tac}$COMT loci. The aroF$^{FBR}$ insert encodes a 3-deoxy-D-arabino-heptulosonic acid 7-phosphate synthase isozyme insensitive to feedback inhibition which increases carbon flow into the common pathway. Due to a mutation in the *E. coli* genomic serA locus required for L-serine biosynthesis, growth in minimal salts medium and plasmid maintenance follows from expression of plasmid-localized serA. The serA insert thus allows microbial growth in minimal salts medium, distinguishing the microbes containing the plasmid from non-plasmid containing microbes.

In an alternative embodiment, the recombinant *E. coli* comprises plasmid pKL5.96A which is identical to plasmid pKL5.97A except for a single P$_{tac}$ COMT locus as compared to the double P$_{tac}$ COMT loci in pKL5.97A.

The above-described preferred recombinant microbe of the present invention, *E. coli* KL7/pKL5.97A, has been deposited with the American Type Culture Collection (ATCC), 1080 University Boulevard, Manassas, Va. 20110-2209, under the terms of the Budapest Treaty, and has been accorded the ATCC designation number 98859. The deposit will be maintained in the ATCC depository, which is a public depository, for a period of 30 years, or 5 years after the most recent request, or for the effective life of a patent, whichever is longer, and will be replaced if the deposit becomes depleted or nonviable during that period. Samples of the deposit will become available to the public and all restrictions imposed on access to the deposit will be removed upon grant of a patent on this application.

The following table sets forth the five enzymes required for the conversion of glucose to vanillic acid, the genes encoding same and the origin of the genes in the exemplary recombinant microbes of the present invention.

TABLE 1

| | Enzyme[†] | Gene (origin) |
|---|---|---|
| a) | 3-deoxy-D-arabino-heptulosonic acid 7-phosphate synthase | aroF$^{FBR}$ (plasmid) |
| b) | 3-dehydroquinate synthase | aroB (additional copy inserted into genome) |
| c) | 3-dehydroquinate dehydratase | aroD (genomic) |
| d) | 3-dehydroshikimate dehydratase | aroZ (inserted into genome) |
| e) | catechol-O-methyltransferase (COMT) | P$_{tac}$ COMT (plasmid) |

Figure 2:
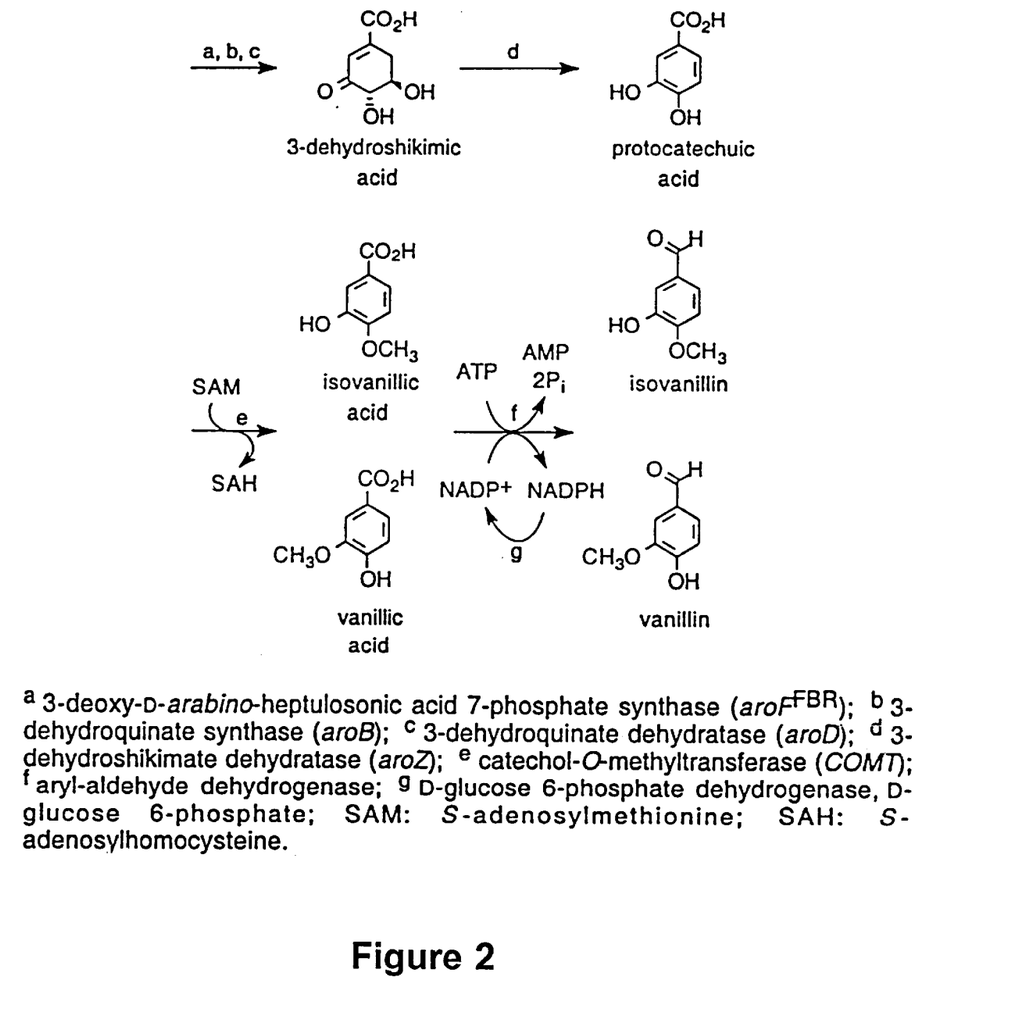
FIG. 2 is a schematic illustrating the synthesis scheme of the present invention.

[†]Enzymes a)–e) correspond to a–e of FIG. 2.

Although *E. coli* is specifically described herein as the microbe for carrying out the methods of the present invention, it will be appreciated that any microorganism such as the common types cited in the literature and known to those skilled in the art, may be employed, provided the microorganism can be altered to effect the desired conversion (e.g., carbon source to vanillic acid, carbon source to 3-dehydroshikimic acid, carbon source to protocatechuic acid, vanillic acid to vanillin, 3-dehydroshikimic acid to vanillin, protocatechuic acid to vanillin, etc.) Thus, it is envisaged that many types of fungi, bacteria and yeasts will work in the methods of the present invention. Such microorganisms may be developed, for example, through selection, mutation, and/or genetic transformation processes with the characteristic and necessary capability of converting one constituent of the synthesis scheme of the present invention to another. Methods for such development are well known to the skilled practitioner.

In order to carry out the bioconversion methods of the present invention, a solution containing a carbon source is contacted with the recombinant microbe to form a bioconversion mixture which is maintained under appropriate conditions to promote the conversion of the carbon source to the desired constituent, e.g., vanillic acid. In a preferred embodiment, the bioconversion mixture is maintained at a temperature of about 30° C. to about 37° C. and a pH of about 6.5 to about 7.5. It is preferred that the bioconversion mixture also contain other substances necessary to promote the viability of the recombinant microbes such as mineral salts, buffers, cofactors, nutrient substances and the like. Methionine (L, D and L-D mixtures) may also be added to the bioconversion mixture. The bioconversion mixture is preferably maintained in a steady state of dissolved oxygen concentration and thus is kept under glucose limited conditions, wherein the rate of glucose addition is determined by the level of dissolved oxygen concentration. A preferred steady state over the course of fermentation is about 100 to about 200 μmol glucose or a dissolved oxygen concentration of about 5% to about 35% air saturation. The more general requirements for the maintenance of viability of microorganisms are well known and specific requirements for maintaining the viability of specific microorganisms are also well known as documented in the literature, or are otherwise easily determined by those skilled in the art. The vanillic acid may then be recovered from the bioconversion mixture by methods known in the art (e.g., organic extraction), and contacted with aryl-aldehyde dehydrogenase to produce vanillin.

In order to more fully demonstrate the advantages arising from the present invention, the following examples are set forth. It is to be understood that the following is by way of example only and is not intended as a limitation on the scope of the invention.

SPECIFIC EXAMPLE 1

Synthesis Of Vanillin From Glucose

I. Results

Figure 3:
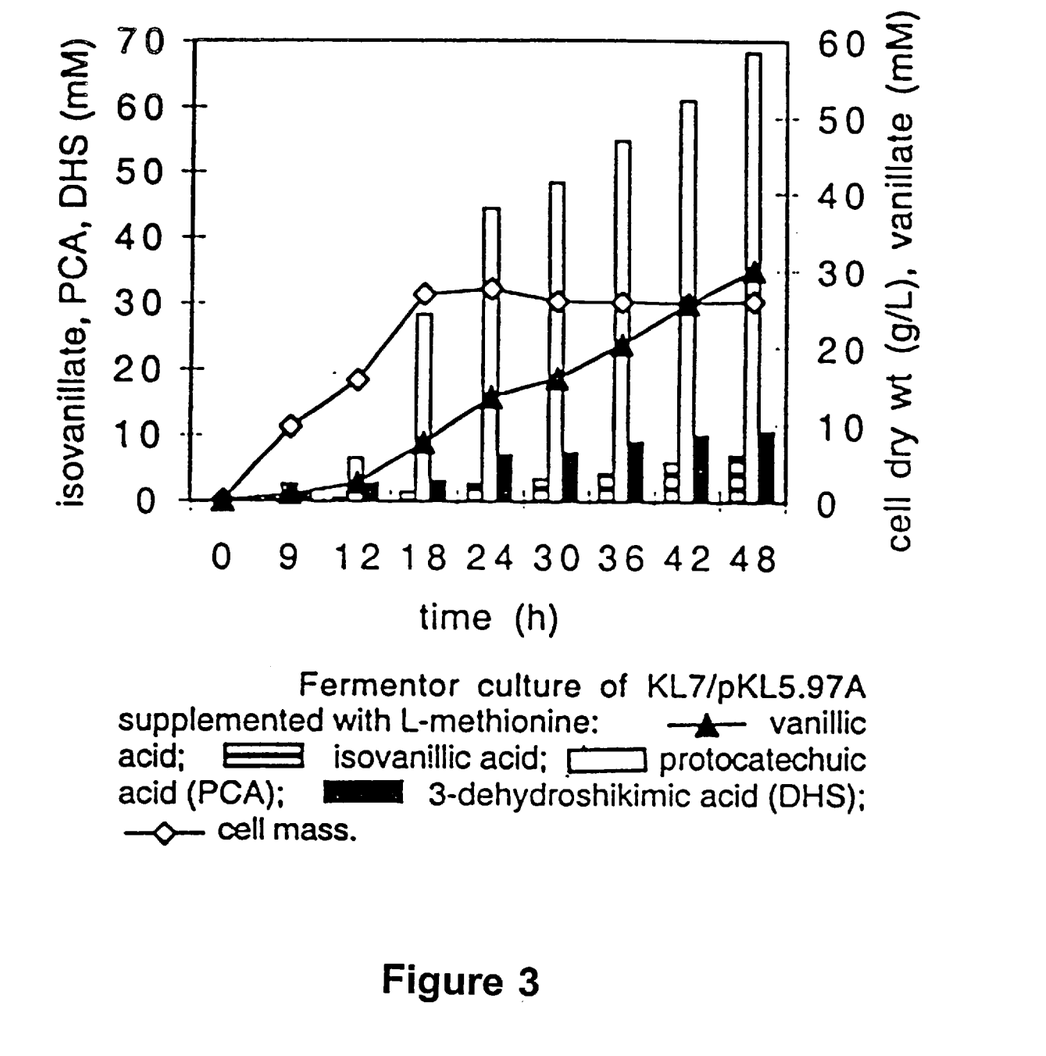
FIG. 3 is a graph showing the effect over time of extracellular accumulation of various constituents on cells (g/L) and vanillate (mM)

KL7/pKL5.26A and KL7/pKL5.97A were cultured for 48 h under fed-batch fermentor conditions at 37° C., pH 7.0, and dissolved oxygen at 20% of saturation. Extracellular accumulation (FIG. 3) of vanillic, isovanillic, protocatechuic, and 3-dehydroshikimic acids began in mid log phase of microbial growth. 3-Dehydroshikimic acid usually constituted 5–10 mol % of the total product mixture indicating that the rates for its biosynthesis and dehydration were nearly equal. However, the molar dominance of protocatechuic acid (FIG. 3, Table 2) relative to vanillic acid pointed to inadequate catechol-O-methyltransferase activity. Although increasing the specific activity (Table 2) of catechol-O-methyltransferase in KL7/pKL5.97A relative to KL7/pKL5.26A had little impact on the concentrations (Table 2) of synthesized vanillic acid, supplementation with L-methionine nearly doubled the amount of vanillic acid synthesized by both biocatalysts (Table 2). The 4-fold to 6-fold molar excess of vanillic acid synthesized relative to isovanillic acid (Table 2) conforms to the reported selectivity of catechol-O-methyltransferase towards meta-hydroxyl group methylation.

TABLE 2

Products formed after 48 h under fed-batch fermentor conditions as a function of catechol-O-methyltransferase activity and L-methionine supplementation.

|  | KL7/pKL5.26A[a] | | KL7/pKL5.97A[b] | |
| --- | --- | --- | --- | --- |
| L-methionine[c] | − | + | − | + |
| COMT[d] | 0.0060 | 0.0055 | 0.012 | 0.010 |
| vanillic acid[e] | 2.5 | 4.9 | 3.0 | 5.0 |
| Isovanillic acid[e] | 0.4 | 1.3 | 0.6 | 1.2 |

TABLE 2-continued

Products formed after 48 h under fed-batch fermentor conditions as a function of catechol-O-methyltransferase activity and L-methionine supplementation.

|  | KL7/pKL5.26A[a] | | KL7/pKL5.97A[b] | |
| --- | --- | --- | --- | --- |
| protocatechuic acid[e] | 9.7 | 7.1 | 12.9 | 10.5 |
| 3-dehydroshikimic acid[e] | 0.9 | 1.0 | 1.0 | 1.8 |

[a]aroF$^{FBR}$P$_{tac}$COMTserA
[b]aroF$^{FBR}$P$_{tac}$COMTP$_{tac}$COMTserA
[c]0.4 g/L added every 6 h beginning at 12 h
[d]specific activity: μmol/min/mg
[e]g/L Aryl-aldehyde dehydrogenase (Gross, G. G. et al., Biochem. Biophy. Res. Commun. 32:173 (1968); Gross, G. G. et al., Eur. J. Biochem. 8:413 (1969); Gross, G. G., Eur. J. Biochem. 31:585 (1972); Zenk, M. H. et al., Recent Adv. Phytochem. 4:87 (1972)) in Neurospora crassa mycelial extract was purified away from an unwanted dehydrogenase which reduced vanillin to vanillyl alcohol. Vanillic, protocatechuic, and isovanillic acids were extracted into EtOAc after acidification of fermentor broth. A subsequent reprecipitation step increased the vanillic acid/protocatechuic acid ratio from 1:2 to 2.5:1 (mol/mol). The resulting aromatic mixture was incubated with glucose 6-phosphate dehydrogenase (to recycle NADP$^+$) and aryl-aldehyde dehydrogenase at 30° C. and pH 8.0 using 0.07 equiv of NADP$^+$ and 2 equiv of ATP relative to vanillic acid. Reduction of vanillic acid to vanillin (FIG. 2) proceeded in 92% yield in 7 h. Reduction of protocatechuic acid was slower with a 33% yield of protocatechualdehyde obtained after 7 h. Vanillin was extracted from the enzymatic reduction with CH$_2$Cl$_2$ leaving protocatechualdehyde and protocatechuic acid in the aqueous phase. Isovanillin at 10 mol % remained as the only contaminant. Extraction of the fermentor broth, selective precipitation to remove excess protocatechuic acid, aryl-aldehyde dehydrogenase reduction, and the final CH$_2$Cl$_2$ extraction led to a 66% overall yield (mol/mol) for conversion of vanillic acid into vanillin.

II. Materials and Methods

General. For $^1$H NMR quantitation of solute concentrations, solutions were concentrated to dryness under reduced pressure, concentrated to dryness one additional time from D$_2$O, and then redissolved in D$_2$O containing a known concentration of 3-(trimethylsilyl)propionic-2,2,3,3-d$_4$ acid (TSP) purchased from Lancaster Synthesis Inc. Concentrations were determined by comparison of integrals corresponding to each compound with the integral corresponding to TSP (δ=0.00 ppm) in the $^1$H NMR. All $^1$H NMR spectra were recorded on a Varian VXR-300 FT-NMR Spectrometer (300 MHz). HPLC analyses employed a Rainin instrument, isocratic elution (17:2:1 H$_2$O/CH$_3$CN/CH$_3$CO$_2$H v/v), a C18 column (5 μm, Rainin Microsorb-MV™, 4.6×250 mm), and detection measured at 250 nm. Samples were quantitated by comparison of the peak area of each component with a standard curve. Protein concentrations were determined using the Bradford dye-binding procedure (Bradford, M. M., Anal. Biochem. 72:248 (1976)) by comparison with a standard curve prepared from bovine serum albumin. Protein assay solution was purchased from Bio-Rad.

Enzyme Assays. A modification of the method of Reenilä was used for assay of catechol-O-methyltransferase activity. Reenilä, I. et al., T. Pharmacol. Toxicol. 77:414 (1995). The cells were washed twice with sodium phosphate (10 mM, pH 7.4) containing dithiothreitol (0.5 mM) and resuspended in sodium phosphate (10 mM, pH 7.4) containing dithiothreitol (0.5 mM). The cells were disrupted by two passages through a French press (16000 psi). Cellular debris was removed by centrifugation at 48000 g for 20 min. Cellular lysate was diluted in sodium phosphate (10 mM, pH 7.4) containing dithiothreitol (0.5 mM).

Two different solutions were prepared and incubated separately at 37° C. for 3 min. The first solution (4 mL) contained sodium phosphate (125 mM) pH 7.4, $MgCl_2$ (6.25 mM), S-adenosyl-L-methionine (0.75 mM), and protocatechuic acid (0.5 mM). The second solution (1 mL) consisted of the diluted lysate containing catechol-O-methyltransferase. After the two solutions were mixed (time=0), aliquots (0.5 mL) were removed at timed intervals (1 min) and quenched with 40 μL ice-cold 4 M perchloric acid. Precipitated protein was removed by centrifugation using a Beckman microfuge and components in the resulting supernatant quantitated by HPLC. One unit of catechol-O-methyltransferase activity was defined as the formation of 1 μmol of vanillic acid and isovanillic acid per min at 37° C.

Aryl-aldehyde dehydrogenase assay solution (1 mL) containing Tris-HCl (100 mM) pH 8.0, $MgCl_2$(10 mM), dithiothreitol (20 mM), NADPH (0.15 mM), ATP (20 mM), and benzoic acid (4 mM) was incubated at 30° C. After addition of solution containing aryl-aldehyde dehydrogenase, benzoic acid reduction was monitored at 340 nm using a Hewlett Packard 8452A UV-Vis spectrophotometer. One unit of activity is defined as the loss of 1 μmol of NADPH per min at 30° C.

Purification of Aryl-aldehyde Dehydrogenase. Whatman (diethylaminoethyl)cellulose (DE52) and Amicon Dye Matrex Red A gels were used during the purification. Buffers included buffer A, Tris-HCl (100 mM) and L-cysteine (10 mM), pH 7.6; buffer B, Tris-HCl (50 mM), EDTA (1 mM), DTT (1 mM), and PMSF (0.4 mM), pH 7.6; buffer C, Tris-HCl (50 mM), EDTA (1 mM), DTT (1 mM), PMSF (0.4 mM), and KCl (400 mM), pH 7.6; buffer D, Tris-HCl (20 mM), EDTA (0.4 mM), DTT (0.4 mM), and PMSF (0.15 mM), pH 7.5; and buffer E, Tris-HCl (20 mM), EDTA (0.4 mM), DTT (0.4 mM), PMSF (0.15 mM), and KCl (2.5 M), pH 7.5. All protein purification manipulations were carried out at 4° C. Protein solution was concentrated by ultrafiltration (PM-10 Diaflo membranes from Amicon).

All medium for cultivation of *Neurospora crassa* SY 7A was prepared in distilled, deionized water. *N. crassa* SY 7A was obtained from the American Type Culture Collection, ATCC designation number 24740. The solid growth medium (1 L) contained sucrose (20 g), sodium citrate dihydrate (2.5 g), $KH_2PO_4$ (5.0 g), $NH_4NO_3$ (2.0 g), $CaCl_2 \supseteq 2H_2O$ (0.1 g), $MgSO_4$ (0.1 g), biotin (5.0 μg), and trace elements including citric acid monohydrate (5.0 mg), $ZnSO_4 \supseteq 7H_2O$ (5.0 mg), $Fe(NH_4)_2(SO_4)_2 \supseteq 6H_2O$ (1.0 mg), $CuSO_4 \supseteq 5H_2O$ (0.25 mg), $MnSO_4 \supseteq H_2O$ (0.05 mg), $H_3BO_3$ (0.05 mg), $Na_2MoO_4 \supseteq 2H_2O$ (0.05 mg). Difco agar was added to the medium solution at a concentration of 2% (w/v). The liquid growth medium differed from solid growth medium only in the addition of Difco yeast extract (2.0 g/L) and sodium salicylate (1.6 g/L). *N. crassa* SY 7A was grown on solid growth medium at 24° C. for 7 days and a mixture of mycelium and spores was obtained. After suspension in sterilized water, the mixture of mycelium and spores was filtered through sterilized glass wool. The resulting spore suspension was stored at 4° C. Fresh spores stored at 4° C. for less than 2 weeks were inoculated into 2 L liquid growth medium in a 4 L Erlenmeyer flask to give a final concentration of 2.5× $10^6$spores/L. Kirk, T. K. et al., *Arch. Microbiol.* 117:277 (1978). After culturing at rt for 60 h, the mycelium was harvested by filtration and frozen at −20° C.

Yields and specific activities at each step of the purification of aryl-aldehyde dehydrogenase are summarized in Table 3. The specific activity of aryl-aldehyde dehydrogenase could not be determined in crude mycelial extract because of the presence of other dehydrogenase activities. The frozen mycelium (400 g, wet weight) was thawed in 900 mL buffer A and then disrupted with a Waring blender. The debris was removed by centrifugation at 40000 g for 30 min followed by concentration of the supernatant to 200 mL. After dialysis against buffer B (3×), the mycelium extract was applied to a DEAE column (5×23 cm) equilibrated with buffer B. The column was washed with 500 mL of buffer B followed by elution with a linear gradient (1.5 L+1.5 L, buffer B-buffer C). Fractions containing aryl-aldehyde dehydrogenase were combined and concentrated to 30 mL. After dialysis against buffer D (3×), The protein was loaded on a RedA column (2.5×8 cm) equilibrated with buffer D. The column was washed with 200 mL buffer D and eluted with a linear gradient (150 mL+150 mL, buffer D/buffer E). Active fractions were concentrated, quick frozen in liquid nitrogen, and stored at −80° C.

TABLE 3

Purification of aryl-aldehyde dehydrogenase from *N. crassa* SY 7A.

| | total units[a] | specific activity[b] | x-fold purification | yield |
|---|---|---|---|---|
| crude lysate | — | — | — | — |
| DEAE | 58 | 0.072 | 1 | 100% |
| RedA | 55 | 0.52 | 7 | 96% |

[a]1 unit = 1 μmol NADH oxidized/min.
[b]μmol/min/mg

Vanillic Acid Synthesis. Fermentations employed a 2.0 L capacity Biostat MD B-Braun fermentor connected to a DCU system and a Compaq computer equipped with B-Braun MFCS software for data acquisition and automatic process monitoring. The temperature, pH and glucose feeding were controlled with a PID controller. The temperature was maintained at 37° C. pH was maintained at 7.0 by addition of concentrated $NH_4OH$ or 2 N $H_2SO_4$. Dissolved oxygen (D.O.) was measured using a Braun polarographic probe. D.O. was maintained at 20% air saturation over the entire course of the fermentation. Antifoam (Sigma 204) was added manually as needed.

All medium was prepared in distilled, deionized water. LB medium (1 L) contained Bacto tryptone (10 g), Bacto yeast extract (5 g), and NaCl (10 g). Fermentation medium (1 L) contained $K_2HPO_4$ (7.5 g), ammonium iron(III) citrate (0.3 g), citric acid monohydrate (2.1 g), and concentrated $H_2SO_4$ (1.2 mL). The culture medium was adjusted to pH 7 by addition of concentrated $NH_4OH$ before autoclaving. The following supplements were added immediately prior to initiation of the fermentation: D-glucose (20 g), $MgSO_4$ (0.24 g), aromatic amino acids including phenylalanine (0.7 g), tyrosine (0.7 g), and tryptophan (0.35 g), aromatic vitamins including p-aminobenzoic acid (0.01 g), 2,3-dihydroxybenzoic acid (0.01 g), and p-hydroxybenzoic acid (0.01 g), and trace minerals including $(NH_4)_6(Mo_7O_{24}) \supseteq 4H_2O$ (0.0037 g), $ZnSO_4 \supseteq 7H_2O$ (0.0029 g), $H_3BO_3$ (0.0247 g), $CuSO_4 \supseteq 5H_2O$ (0.0025 g), and $MnCl_2 \supseteq 4H_2O$ (0.0158 g). D-Glucose, $MgSO_4$, and aromatic amino acids were autoclaved while aromatic vitamins and trace minerals were sterilized through 0.22 μm membranes prior to addition to the medium. Antibiotics were added where appropriate to the following final concentrations: chloramphenicol (Cm), 20 µg/mL; ampicillin (Ap), 50 µg/mL. Solid medium was prepared by addition of 1.5% (w/v) Difco agar to medium solution.

Inoculants were grown in 100 mL LB medium (enriched with 2 g glucose) containing the appropriate antibiotic for 12 h at 37° C. with agitation at 250 rpm and then transferred to the fermentor. The initial glucose concentration in the fermentation medium was 20 g/L. L-Methionine supplementation, when employed, consisted of addition of a filter-sterilized solution containing 0.4 g of this amino acid in timed intervals (6 h) starting at 12 h after initiation of a fermentor run. Three different methods were used to maintain dissolved oxygen (D.O.) levels at 20% air saturation during each 48 h fermentor run. The dissolved oxygen concentration was first maintained by increasing the impeller speed. Approximately 8 h was required for the impeller speed to increase from 50 rpm to the preset maximum value of 900 rpm. The mass flow controller then maintained D.O. levels at 20% saturation at constant impeller speed by increasing the airflow rate over approximately 2 h from 0.06 L/L/min to a preset maximum of 1.0 L/L/min. At constant impeller speed and constant airflow rate, D.O. levels were maintained at 20% saturation for the remainder of the fermentation by oxygen sensor-controlled glucose feeding. At the beginning of this stage, dissolved oxygen levels fell below 20% saturation due to residual initial glucose in the medium. This lasted for approximately 1 h before glucose (60% w/v) feeding started. The PID control parameters were set to 0.0 (off for the derivative control ($T_D$), 999.9 s (minimum control action) for the integral control ($T_I$), and 950.0% for the proportional band ($X_p$).

Samples (6 mL) of fermentation broth were taken at 6 h intervals. A portion (1 mL) was used to determine cell densities by measurement of absorption at 600 nm ($OD_{600}$). Dry cell weight (g/L) was obtained using a conversion coefficient of 0.43 g/$OD_{600}$L. The remaining 5 mL of each fermentation froth sample was centrifuged using a Beckman microfuge and analyzed by HPLC. A separate aliquot (25 mL) of fermentation broth was taken and centrifuged at 12 h and 36 h for assay of catechol-O-methyltransferase activity. Since stable catechol-O-methyltransferase activity was observed over the course of the fermentation, reported catechol-O-methyltransferase activity (Table 1) is the average of 12 h and 36 h specific activities. After 48 h, cells were removed by centrifugation at 16000 g for 10 min and the supernatant stored at 4° C.

Figure 4:
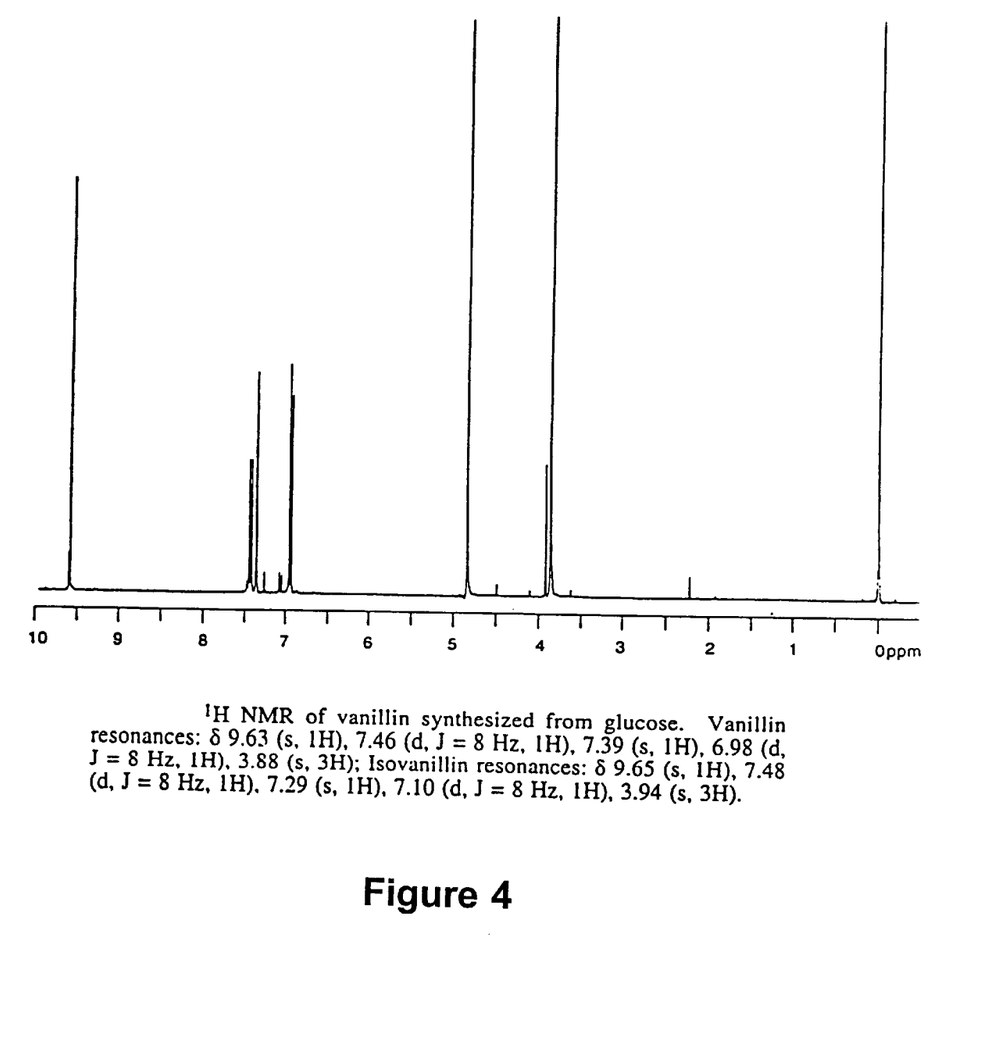
FIG. 4 is a $^1$H NMR of vanillin synthesized from glucose.

Reduction of VanillicAcid. Fermentation broth (100 mL) was acidified to pH 3.1 using concentrated HCl and the resulting precipitated protein was removed by centrifugation at 16000 g for 10 min. After extraction of the supernatant with EtOAc (3×), the solvent was removed under reduced pressure. The resulting solid was dissolved in 12 mL of water adjusted to pH 7.5 by NaOH (10 N) addition. Subsequent dropwise addition of concentrated sulfuric acid acidified the solution to pH 1.8 and resulted in precipitation of a solid which was filtered and dried. The collected precipitate was dissolved in a solution (100 mL) containing Tris-HCl (200 mM), pH 8.0, $MgCl_2$ (100 mM), DTT (10 mM), ATP (60 mM), $NADP^+$ (2 mM), glucose 6-phosphate (60 mM), 2,000 units of glucose 6-phosphate dehydrogenase and 200 unit of the partially purified aryl-aldehyde dehydrogenase. Reduction proceeded at 30° C. and was monitored by HPLC. After 7 h reaction, 92% (mol/mol) of the starting vanillic acid and 34% (mol/mol) of the protocatechuic acid had been reduced. The reaction mixture was extracted with 100 mL $CH_2Cl_2$ (3×). The combined organic extracts were washed one time with equal volume of water. Concentration afforded a powder consisting of (FIG. 4) vanillin (0.30 g) and isovanillin (0.03 g).

SPECIFIC EXAMPLE 2

Commercial Applications

For large-scale vanillin synthesis, an intact microbe (as opposed to cell-free enzyme systems) to reduce vanillic acid is preferred. However, it should be appreciated that irrespective of the strategy employed, improved protocatechuic acid methylation will be essential. The lack of significantly improved protocatechuic acid methylation with increased catechol-O-methyltransferase activity and the improvement in methylation observed with L-methionine supplementation suggest that cosubstrate S-adenosylmethionine availability and/or feedback inhibition (Coward, J. et al., *Biochemistry* 12:2291 (1973)) may be limiting in vivo methyltransferase activity. Improving regioselectivity for protocatechuic acid meta-oxygen methylation using a different isozyme of widely distributed (Gross, G. G. et al., *Biochem. Biophy. Res. Commun.* 32:173 (1968); Gross, G. G. et al., *Eur. J. Biochem.* 8:413 (1969); Gross, G. G., *Eur. J. Biochem.* 31:585 (1972); Zenk, M. H. et al., Recent *Adv. Phytochem.* 4:87 (1972)) catechol-O-methyltransferase is also advantageous. In addition, a vanillate-synthesizing microbe designed with a protocatechuic acid uptake system so that protocatechuic acid escaping into the culture supernatant can be transported back into the cytoplasm for methylation, would also be desirable.

Biocatalytic synthesis of vanillin from a carbon source such as glucose has a number of advantages relative to other biocatalytic vanillin syntheses. Coniferol, formed during phenylpropanoid biosynthesis, is converted into coniferin by a glucosyltransferase in *Vanilla planifolia*. Ranadive, A. S., In *Spices, Herbs, and Edible Fungi*, Charalambous, G., Ed., Elsevier: Amsterdam, p.517 (1994). Coniferin is then transformed into glucovanillin which is finally hydrolyzed by a β-glucosidase. Ranadive, A. S., In *Spices, Herbs, and Edible Fungi*, Charalambous, G., Ed., Elsevier: Amsterdam, p. 517 (1994). Synthesis of vanillin via 3-dehydroshikimic, protocatechuic, and vanillic acids as taught by the present invention, circumvents phenylpropanoid biosynthesis and glucosylation/deglucosylation reactions. This substantially reduces the number of enzymes required to synthesize vanillin.

Biocatalytic synthesis of vanillin from a carbon source such as glucose also has advantages relative to synthetic vanillin manufacture. Esposito, L. et al., *Kirk-Othmer Encyclopedia of Chemical Technology*, Fourth Ed., Kroschwitz, J. 1.; Howe-Grant, M., Ed.; Wiley: New York, Vol. 24:812 (1997). Phenol and guaiacol are toxic and are derived from carcinogenic benzene. Lewis, R. J. Sr., *Hazardous Chemicals Desk Reference*, Third Edition, Van Nostrand Reinhold: New York (1993). The nontoxic 3-dehydroshikimic, protocatechuic, and vanillic acids of the methods of the present invention are derived from innocuous glucose. Corrosive $H_2O_2$ used for oxidation of phenol into catechol requires special handling precautions (Campbell, C. J. et al., *Sci. Am.* 278(3):78 (1998)) while biocatalytically synthesized vanillin derives its oxygen atoms from the oxygen atoms of glucose. Dimethyl sulfate, a carcinogen, (Campbell, C. J. et al., *Sci. Am.* 278(3):78 (1998)) has historically been used to methylate catechol. Protocatechuic acid methylation employs S-adenosylmethionine generated and consumed intracellularly. Finally, synthetic vanillin manufacture is based on use of nonrenewable petroleum whereas glucose is derived from abundant, renewable starch.

This difference in feedstock utilization is important given projected fierce international competition as global petroleum production diminishes. Campbell, C. J. et al., *Sci. Am.* 278(3):78 (1998).

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

Patent and literature references cited herein are incorporated by reference as if fully set forth.

What is claimed is:

1. A method of synthesizing vanillin from a carbon source compsing:
    a) converting the carbon source to vanillic acid with a microbe comprising a recombinant gene encoding a 3-dehydroshikimate dehydratase and a recomnbinant gene encoding catechol-O-methyltransferase; and
    b) reducing the vanillic acid to vanillin with aryl-aldelhyde dehydrogenase.

2. The method of claim 1, wherein the gene encoding 3-dehydroshikimate dehydratase is the aroZ gene.

3. The method of claim 1, wherein the gene encoding catechol-O-methyltransferase is the $P_{tac}$COMT gene.

4. The method of claim 3, wherein the $P_{tac}$COMT gene is located on a plasmid in the microbe.

5. The method of claim 4, wherein the plasmid is pKL5.97A.

6. The method of claim 1, wherein the microbe is *E. coli* KL7/pKL5.97A identified by ATCC designation anmber 98859.

7. The method of claim 1, wherein the microbe further comprises a gene encoding for an isozyme of 3deoxy-D-arabino-heptulosonate-7-phosphate synthase insensitive to feedback inhibition.

8. The method of claim 7, wherein the gene coding for the 3-deoxy-D-arabino-heptulosonate-7-phosphate synthase isozyme is an $aroF^{FBR}$ gene.

9. The method of claim 8, wherein the $aroF^{FBR}$ is located on a plasmid in the microbe.

10. The method of claim 1, wherein the aryl-aldehyde dehydrogenase is purified from *Neurospora crassa*.

11. The method of claim 1, wherein the carbon source is glucose.

12. A method of synthesizing vanillin from a carbon source comprising:
    a) converting the carbon source to vanillic acid with an *E. coli* comprising recombinant genes encoding 3-deoxy-D-arabino-heptulosonic acid 7-phosphate synthase, 3-dehydroquinate synthase, 3-dehydroquinate synthase (aroB), 3-dehydroquinate dehydratase, 3-dehydroshikimate dehydrates and catechol-O-methyltransfiemse; and
    b) reducing vanillic acid to vanillin with arylaldehyde dehydrogenase.

13. The method of claim 12, wherein the *E. coli* comprises a mutated aroE locus encoding shikimate dehydrogenase, an aroB/aroZ cassette inserted into a serA locus, and plasmid p5.97A.

14. The method of claim 12, wherein the aryl-aldehyde dehydrogenase is purified from *Neurospora crassa*.

15. The method of claim 12, wherein the *E. coli* is KL7/pKL5.97A identified by ATCC designation number 98859.

16. The method of claim 12, wherein the carbon source is glucose.

17. A process for the production of vanillin comprising:
    a) contacting a bioconversion mixture comprising a carbon source with a microbe comprising a recombinant gene encoding a 3-dehydroshilcimate dehydratase and a recombinant gene encoding catechol-O-methyltransferase, wherein the microbe converts the carbon source to vanillic acid; and
    b) contacting the vanillic acid with aryl-aldehyde dehydrogenase, wherein the aryl-aldehyde dehydrogenase reduces the vanillic acid to vanillin.

18. The process of claim 17, wherein the microbe is *E. coli* comprising a mutated aroE locus, an aroB/aroZ cassette inserted into the serA locus and plasmid pKL5.97A.

19. The process of claim 17, wherein the aryl-aldehyde dehydrogenase is purified from *Neurospora crassa*.

20. The process of claim 17, wherein the microbe is *E. coli* KL7/pKL5.97A identified by ATCC designation number 98859.

21. The process of claim 17, wherein the carbon source is glucose.

22. The process of claim 17, wherein the bioconversion mixture is maintained at a temperature of about 30° C. to about 37° C. and a pH of about 6.5 to about 7.5.

23. The process of claim 17, wherein the bioconversion mixture has a dissolved oxygen concentration of about 5% to about 35% air saturation.

24. The process of claim 17, wherein the steps are performed in a fed-batch fermentor.

25. *E. coli* KL7/pKL5.97A identified by ATCC designation number 98859.

26. Plasmid pKL5.97A.

* * * * *

UNITED STATES PATENT AND TRADEMARK OFFICE
CERTIFICATE OF CORRECTION

PATENT NO.   : 6,372,461 B1
DATED        : April 16, 2001
INVENTOR(S)  : Frost

It is certified that error appears in the above-identified patent and that said Letters Patent is hereby corrected as shown below:

Title page,
Item [56], References Cited, U.S. PATENT DOCUMENTS, delete "5,279,950  A  1/1994 Laduda et al." and insert -- 5,279,950  A  1/1994 Labuda et al. --.

Column 6,
Line 27, delete "25".

Column 8,
Line 11, delete "supematant" and insert -- supernatant --.

Column 11,
Line 19, delete "recomnbinant" and insert -- recombinant --.
Line 33, delete "anmber" and insert -- number --.
Line 36, delete "3deoxy-D-" and insert -- 3-deoxy-D- --.
Line 42, after "aroF$^{FBR}$" insert -- gene --.

Column 12,
Line 2, delete first occurrence of "3-dehydroquinate synthase,".
Line 4, delete "dehydrates" and insert -- dehydratase --.
Line 5, delete "methyltransfiemse" and insert -- methyltransferase --.
Line 6, delete "aryladehyde" and insert -- aryl-aldehyde --.
Line 22, delete "3-dehydroshilcimate" and insert -- 3-dehydroshikimate --.

Signed and Sealed this

Eighteenth Day of March, 2003

JAMES E. ROGAN
*Director of the United States Patent and Trademark Office*

UNITED STATES PATENT AND TRADEMARK OFFICE
CERTIFICATE OF CORRECTION

PATENT NO.         : 6,372,461 B1
APPLICATION NO.    : 09/397720
DATED              : April 16, 2002
INVENTOR(S)        : John W. Frost It is certified that error appears in the above-identified patent and that said Letters Patent is hereby corrected as shown below:

In the Specification

Column 1, Line 6, delete "Work on this invention was sponsored in part by the United States Department of Agriculture Grant No. 95-37500-1930 and the National Science Foundation Grant No. CHE963368 amendment 002. The Government may have certain rights in the invention." and insert therefor; --This invention was made with government support under CHE9633682 awarded by the National Science Foundation and 95-37500-1930 awarded by the United States Department of Agriculture. The government has certain rights in the invention.--

Signed and Sealed this
Twenty-fifth Day of February, 2014

Michelle K. Lee
*Deputy Director of the United States Patent and Trademark Office*